(12) United States Patent
De La Prieta et al.

(10) Patent No.: US 6,716,327 B1
(45) Date of Patent: Apr. 6, 2004

(54) MEASURING ARRANGEMENT FOR THE DETERMINATION OF GAS COMPONENTS IN A GAS MIXTURES

(75) Inventors: Claudio De La Prieta, Stuttgart (DE); Gerhard Hoetzel, Stuttgart (DE); Carmen Schmiedel, Marbach am Neckar (DE); Petra Kitiratschky, Leonberg (DE); Thomas Schulte, Gerlingen (DE); Hans-Dieter Wiemhoefer, Münster (DE)

(73) Assignee: Robert Bosch GmbH, Stuttgart (DE)

( * ) Notice: Subject to any disclaimer, the term of this patent is extended or adjusted under 35 U.S.C. 154(b) by 354 days.

(21) Appl. No.: 09/254,402
(22) PCT Filed: Aug. 8, 1997
(86) PCT No.: PCT/DE97/01683
§ 371 (c)(1), (2), (4) Date: Sep. 24, 1999
(87) PCT Pub. No.: WO98/10275
PCT Pub. Date: Mar. 12, 1998

(30) Foreign Application Priority Data

Sep. 2, 1996 (DE) .......................................... 196 35 494
Dec. 19, 1996 (DE) .......................................... 196 52 968

(51) Int. Cl.[7] ............................................. G01N 27/407
(52) U.S. Cl. ........................ 204/426; 204/415; 204/427
(58) Field of Search .............................. 204/421–429, 204/415

(56) References Cited

U.S. PATENT DOCUMENTS 5,178,744 A * 1/1993 Nakazawa et al. .......... 204/429
5,273,628 A * 12/1993 Liu et al. .................... 204/296
5,397,442 A    3/1995 Wachsman
5,543,025 A    8/1996 Garzon et al.
5,667,652 A * 9/1997 Liu et al. .................... 264/412
5,879,526 A * 3/1999 Dietz et al. ................. 204/426

FOREIGN PATENT DOCUMENTS

| DE | 37 28 618 | 3/1988 |
|----|-----------|--------|
| DE | 44 39 901 | 5/1996 |
| EP | 0 468 500 | 1/1992 |
| EP | 0 678 740 | 10/1995 |
| EP | 0 769 694 | 4/1997 |
| GB | 2 287 543 | 9/1995 |

OTHER PUBLICATIONS

Liu et al, "Oxygen Sensors", ASM Engineered Materials Handbook, vol. 4, Ceramics and Glasses, pp. 1131–1139, (1991).*
Liu, "Theretical Assessment of Oxygen Separation Rates of Mixed Conduction", Ionic and Mixed Conducting Ceramics, pV–91–12, pp. 95–109, (1991).*
N. Kato, et al., "Thick Film ZrO2 $No_x$ Sensor", SAE, pp. 137–142, (1996).

* cited by examiner

Primary Examiner—T. Tung
(74) Attorney, Agent, or Firm—Kenyon & Kenyon

(57) ABSTRACT

A measuring arrangement for the analysis of gas components in gas mixtures, having at least one electrochemical solid electrolyte test cell with at least one cathode in a diffusion channel is exposed to a gas mixture. The use of several cathodes wired one behind the other makes possible selective analysis of individual gas components. At the first cathode, oxygen is selectively pumped off by the use of specifically oxygen-ion-conductive layers so that another component of the gas mixture can be analyzed by the following electrode.

10 Claims, 2 Drawing Sheets

MEASURING ARRANGEMENT FOR THE DETERMINATION OF GAS COMPONENTS IN A GAS MIXTURES

FIELD OF THE INVENTION

The present invention relates to a measuring arrangement, in particular on the basis of electrochemical sensors, for the an analysis of gas components in gas mixtures, in particular in exhaust gases of internal combustion engines, to.

BACKGROUND INFORMATION

It is known that exhaust gases of combustion engines, for example diesel engines, in addition to uncombusted fuel components and oxygen also contain nitrogen oxides and other gases. The composition of the exhaust gas is determined to a significant degree by the adjustment of the fuel-air mixture at which the internal combustion engine is operated. If, for example, fuel is present in stoichiometric excess, considerable quantities of uncombusted or only partially combusted fuel are present in the exhaust gas, while in the case of a stoichiometric excess of air oxygen in the fuel-air mixture, a correspondingly higher concentration of oxygen will be present in the exhaust gas. The analysis of the composition of the exhaust gas with a limit current sensor e.g. (Lambda sensor) is known as a method for setting an optimal fuel-gas mixture. The limit current sensor has a solid electrolyte arranged between two electrodes, with one electrode being exposed to the exhaust gas via a diffusion barrier. When a constant voltage is applied to the electrodes, a limit current will develop as a result of the difference in oxygen concentration at the two electrodes; this limit current is measured with a measuring arrangement and is evaluated, for example, for setting the fuel-air mixture at which the internal combustion engine is being operated.

A limit current sensor of this kind is described, for example, in German Patent No. 37 28 618. An electrode configured as a pump electrode is arranged in a diffusion channel, which is in contact on one side with the test gas mixture. Arranged in the diffusion channel is a diffusion barrier of such a design that an oxygen partial pressure corresponding to the voltage applied develops at the electrode in contact with the exhaust gas across the diffusion barrier.

German Patent Application No. 44 39 901 describes that a pump electrode for analyzing oxygen partial pressure can be combined with a second electrode for analysis of nitrogen oxides in gas mixtures. In this method the first electrode is covered by a gas-permeable membrane. A further possibility for analysis of additional gas components, in particular nitrogen oxides, in gas mixtures is described in the article by N. Kato, K. Nagakaki, and N. Ina in *SAE* 1996, pages 137 seqq. A particular disadvantage in these conventional methods was the reactivity of the nitrogen oxides and other gas components with parts of the electrode or of the catalyst.

SUMMARY OF THE INVENTION

A measuring arrangement for analysis of gas components in gas mixtures according to the present invention, in particular in exhaust gases of internal combustion engines, is composed of at least one electrochemical solid-electrolyte test cell, the cathode of which is covered with a selectively oxygen-ion-conducting layer that is separated from the cathode by an electrically insulating layer. In this manner any components of the exhaust gas such as sulfur oxides and nitrogen oxides, for example, cannot react with the cathode. In addition, the spatial separation makes it possible for electrically conductive materials to be used as an oxygen-ion-conductive layer without catalytic properties of the oxygen-ion-conductive layer being influenced by the electrical potential that is present on cathode 15 of the pump cell. In this manner oxygen can be selectively removed from the test gas so that other gas components can later be selectively analyzed.

By providing a second cathode that is not covered with an oxygen-ion-conductive layer, additional gas components within the gas stream can be selectively detected after the oxygen is pumped out. This applies in particular to the detection of nitrogen oxides or hydrocarbons or sulfur oxides which can be analyzed through appropriate selection of electrode for the second electrode, i.e., the second cathode. It is also advantageous that the pump capacity of the first oxygen pump cell can be set through the structure and thickness of the oxygen-ion-conductive layer. For example, it is conceivable for the method to be optimized such that all of the oxygen can be pumped off quickly and individual gas components of the gas mixture can be analyzed in the additional electrodes provided.

In one embodiment according to the present invention the oxygen-ion-conductive layer is composed of a mixed-conductive ceramic material. For example, compounds such as mixed-conductive metal oxides, preferably their structural variants doped with rare earth elements such as perovskites or elpasolites, but also cuprites, ferrites, and cobaltites, are used.

The oxygen-ion-conductive layer can be composed of catalytically active mixed metal oxide making it possible to use the pump cell as a lambda sensor since the equilibrium oxygen is determined.

Another embodiment of the present invention facilitates a use of mixed ion-conductive metal oxides which does not cause any change in the gas components, with the result that the free oxygen which has not reacted in equilibrium is measured. This makes it possible, for example, to diagnosis in a preferred, simple manner the quality, performance, and condition of the catalyst, for example, a catalyst for gas mixtures of internal combustion engines.

In another embodiment, it is possible to use mixed-conductive oxides which permit selective gas reactions on their surface providing a further selection possibility for various gas components, for example, nitrogen oxides in the gas mixture.

In another embodiment, the diffusion channel is arranged in a heat-resistant glass with the result that in a post-firing assembly process, all parts of the measuring arrangement can be constructed separately and joined together at low temperatures. In addition, the use of heat-resistant glass has the result that any gas components will not be able to react or will react only with difficulty with the material in which the diffusion channel is arranged, as is the case, for example, with conventional ceramics.

In another embodiment, the entire measuring arrangement can be heated so that the operating temperature is attained relatively quickly and thus even complex gas mixtures can be analyzed in a short time.

Another embodiment of the present invention also enables manufacturing the multilayer measuring arrangement in the post-firing process making it possible to use numerous material combinations which cannot otherwise be combined, for example in a co-firing assembly process as a result of the high temperature, since parts of the multilayer setup would decompose earlier. A co-firing assembly process is also possible in the case of the measuring arrangement according to the present invention with the proper selection of materials.

DETAILED DESCRIPTION

Figure 1:
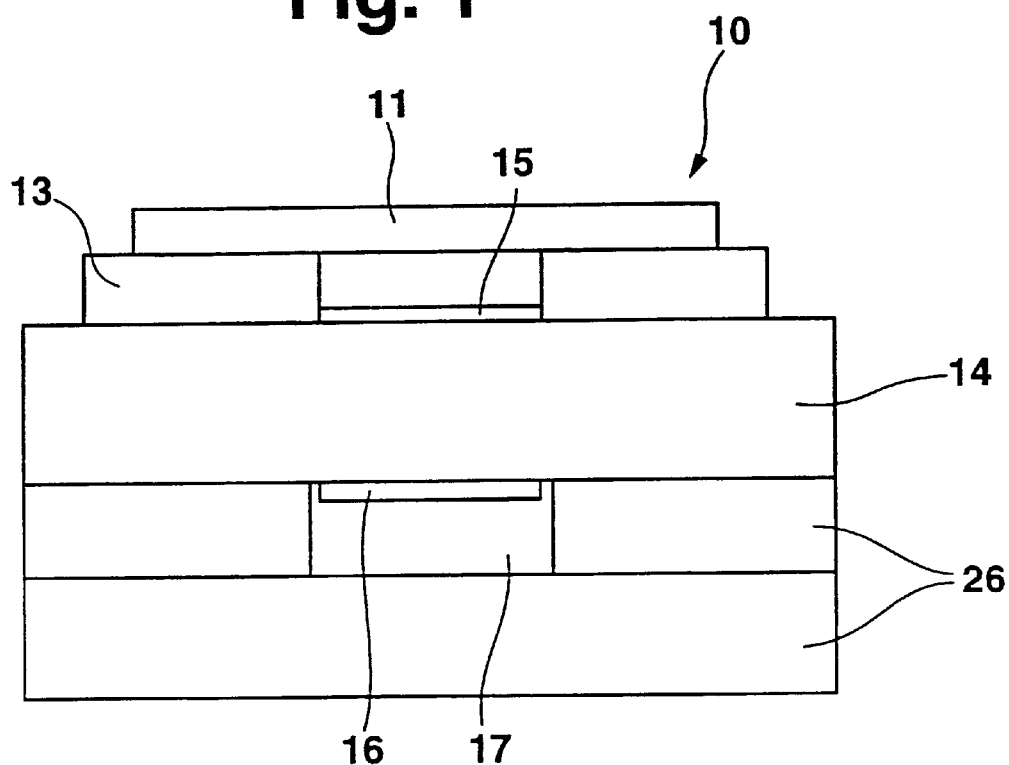
FIG. 1 shows a cross section and a multilayer structure of a measuring arrangement according to the present invention which includes a first cathode.

FIG. 1 shows a measuring arrangement designated generally as 10. Measuring arrangement 10 has an essentially disk-shaped solid electrolyte 14 on the side of which electrode 16 is arranged which is wired as an anode. On the side of solid electrolyte 14, composed for example of zirconium dioxide/yttrium oxide ceramic, across from anode 16 is an electrode 15 wired as a cathode. Cathode 15 is covered with a gas-tight layer 13, composed for example of α- or γ-aluminum oxide, which, in zone 12 above the cathode, is gas permeable. This electrically insulating layer 12, 13 is covered with an additional layer 11 composed of a mixed-conductive metal oxide, for example a perovskite such as $La_{0.6}Sr_{0.4}Co_{0.8}Cu_{0.2}O_{3-\delta}$ or $Gd_{0.7}Ca_{0.3}FeO_{3-\delta}$. The thickness of layer 12, 13 varies between 5 and 200 µm. Both anode 16 and cathode 15 are connected via a strip conductor (not depicted) to terminals of measuring arrangement 10 (also not depicted). Electrodes 15, 16 are preferably composed of platinum or another corrosion-resistant metal or a metal alloy. Below anode 16, a diffusion channel 17 is positioned through which reference air can be brought to the anode. Diffusion channel 17 for reference air is positioned in a multilayer body composed of several layers 26 of zirconium dioxide, for example.

Figure 2:
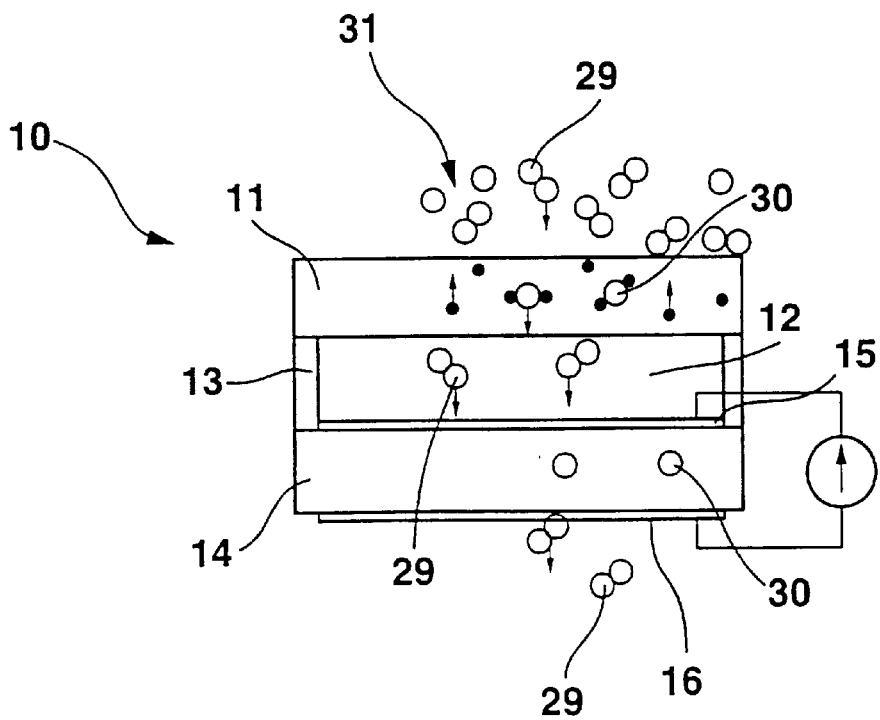
FIG. 2 shows a mode of operation of the measuring arrangement illustrated in FIG. 1.

FIG. 2 shows the principle of operation of the measuring arrangement illustrated in FIG. 1. A gas mixture 31 is brought to measuring arrangement 10. In this gas mixture 31, there are $O_2$ molecules 29 which are pumped off and diffused through oxygen-ion-conductive layer 11 in the form of $O^{2-}$ ions 30, recombining at phase boundary 11, 12 into molecular oxygen 29. There they are detected in a known manner by pump electrode 15 and are quantitatively analyzed using the pump current. The other components of gas mixture 31 are not conducted through selectively oxygen-ion-conductive layer 11.

Figure 3:
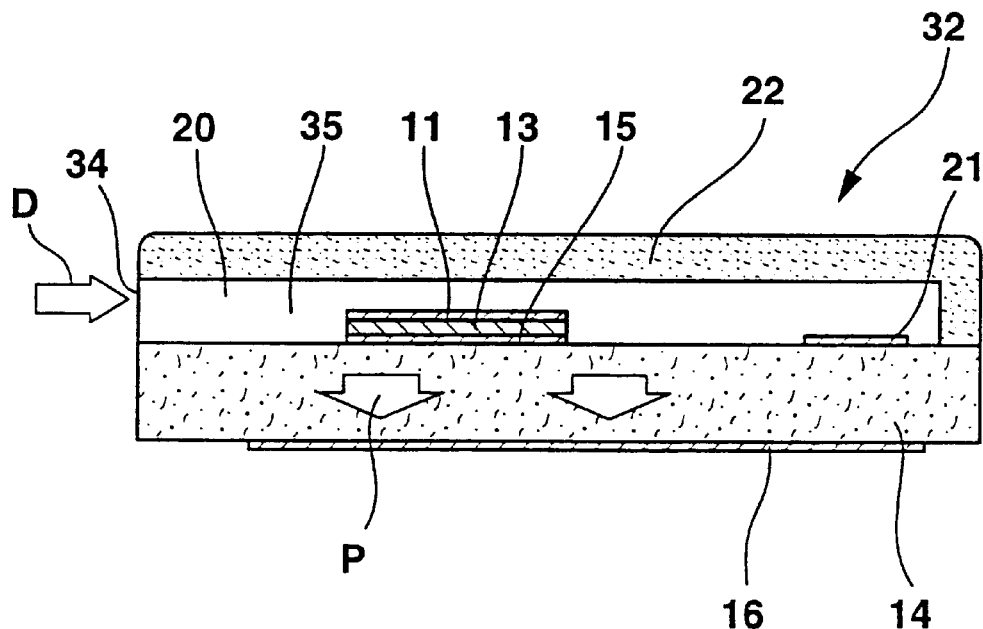
FIG. 3 shows another exemplary embodiment of the measuring arrangement.

FIG. 3 shows one exemplary embodiment of a measuring arrangement for selective analysis of two components in a measured gas. Sensor 32 has an essentially plate-like solid electrolyte 14, on one side of which is arranged electrode 16, which is wired as an anode. On the side of solid electrode 14 across from anode 16, an electrode 15 wired as a cathode is arranged, which is covered with an insulating layer 12, 13 and with a selectively oxygen-ion-conductive material 11. Second cathode 21 is arranged in diffusion channel 20 downstream from first electrode 15. Both anode 16 and cathodes 15 and 21 are connected via strip conductors (not depicted) to terminals of sensor 32 (likewise not depicted). The electrodes are porous and permeable to gas and can, for example, be composed of platinum. Solid electrolyte 14 is composed, by way of example, of a zirconium oxide stabilized with yttrium oxide. Cathodes 15 and 21 are arranged in diffusion channel 20. Diffusion channel 20 has an opening 34 on one side and is closed at its other side. Diffusion channel 20 thus forms a blind recess. In order to form diffusion channel 20, sensor 32 has a covering 28 which is arranged as a layer over solid electrolyte 14 and a recess which forms diffusion channel 20. Cathode 15 is arranged in diffusion channel 20 close to opening 34, while second cathode 21 is arranged away from opening 34. First cathode 15 is thus arranged between opening 34 and second cathode 21.

The sensor is exposed to a gas mixture, for example the exhaust gas of an internal combustion engine. For this purpose, sensor 32 has holding means (e.g. a holding arrangement) not shown in the figure. The gas mixture is present at anode 16 and in diffusion channel 20, indicated with arrow D. Covering 28 is configured to be gas-tight so that gas mixture 31 can enter diffusion channel 20 only through opening 34. Gas mixture 31 typically contains primarily oxygen and nitrogen oxides as well as other components. In diffusion chamber 20, a diffusion barrier 35 is arranged which is preferably porous. In the event of a change in the composition of the gas mixture, diffusion barrier 35 prevents it from being present simultaneously at anode 16 and at cathodes 15 and 21. Since cathode 15 is arranged upstream from cathode 21 in diffusion channel 20, gas mixture 31 comes to cathode 21 only if it has first passed by cathode 15. Coating 11 is permeable exclusively for oxygen in the form of oxygen ions so that the additional components still present in gas mixture 31 such as nitrogen oxides or hydrocarbons cannot reach cathode 15. In the case of the sensor depicted in FIG. 3, a heating device, which heat sensors of this kind possess as a rule, is not depicted for the sake of clarity. The heating device serves to warm sensor 32 to a necessary operating temperature of several hundred degrees C.

Figure 4:
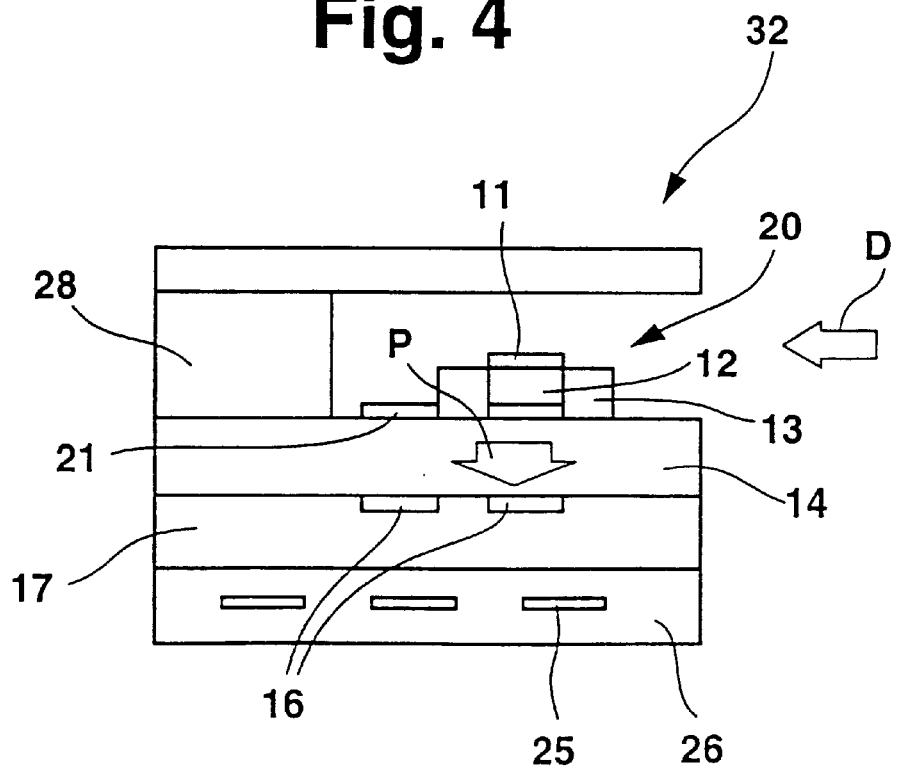
FIG. 4 shows still another exemplary embodiment of the measuring arrangement.

Another embodiment of a sensor 32 is shown in FIG. 4. The material of covering 28 is composed of a heat-resistant material, for example a chemically or thermally resistant glass and/or glass ceramic. A glass or a glass ceramic, the chemical composition of which can be that of the material of covering 28, serves as a gas-tight closure of insulating coating 12, which is gas permeable in zones, and at the same time serves as additional insulating layer 13. Sensor 32 can be produced with a few printing steps which are known as such and are controllable, for example in silk-screen printing, and the individual components of layers 26, 14, 16, and 28 can be applied and joined to each other both in co-firing and in post-firing processes. In particular, the use of a glass-like covering 28 makes manufacture using the post-firing process possible.

A heating element 25 is arranged in an additional layer 26 of aluminum oxide, for example.

Sensor 32 shown in FIGS. 3 and 4 performs the following functions:

During the operation of sensor 32, a pumping voltage is applied between first cathode 15 and anode 16. Between cathode 21 and anode 16 there is another voltage, which is separated from the pumping voltage by circuit engineering means. Gas mixture 31 diffuses through diffusion channel 20 past coating 11 of first cathode 15. Since coating 11 is selective exclusively for oxygen ions, oxygen diffuses to cathode 15 through the spatially separated, electrically insulated layer 12, causing layer 11 to be voltage-free. As a result of the pumping voltage applied between cathode 15 and anode 16, oxygen $O_2$ is pumped out of gas mixture 31. In this process, the following transformation reaction takes place:

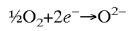

Oxygen $O_2$, as is indicated in the figure with arrows P, is pumped as oxygen ion $O^{2-}$ from cathode 15 to anode 16 through solid electrolyte 14, so that a pumping current flows across solid electrolyte 14. The pumping current can be measured using a not-depicted measuring instrument, for example, an ammeter, and forms a reference point for oxygen concentration present in gas mixture 31. Gas mixture 31, which enters into diffusion channel 20, now diffuses past cathode 15 to cathode 21. As a result of the described pumping of oxygen $O_2$ out of gas mixture 31, a gas mixture essentially freed of oxygen $O_2$ is present at cathode 21. This gas mixture thus contains essentially only components such as nitrogen oxides, hydrocarbons, etc. Through the voltage applied to cathode 21 and anode 16, a limit current signal develops, which, for example, depends exclusively upon the concentration of nitrogen oxide in gas mixture 31. This limit current signal can be evaluated using a measuring device, for example, an ammeter.

Therefore, sensor 32 is suitable for detecting an oxygen concentration on the one hand and for detecting an additional component of gas mixture 31 independently of each other. Because oxygen is pumped out of gas mixture 31 before such gas mixture 31 reaches second cathode 21, nitrogen oxides, for example, can be quantitatively analyzed in gas mixture 31 even in small quantities.

Another embodiment of the measuring arrangement according to the present invention involves coating second electrode 21 with a material, for example, appropriately doped mixed metal oxides or appropriately doped binary and ternary mixtures of nonmetals and metals, which is selectively permeable for saturated and/or saturated hydrocarbons or sulfur dioxide or nitrogen oxides. As a result, in a further embodiment (not depicted), several cathodes arranged sequentially in a diffusion channel 20, each with a specifically sensitive coating, can detect various components of the gas mixture.

The areas of application of sensor 32 can be summarized as follows based on the nature of the oxygen-ion-conductive metal oxide:

1. Oxygen-ion-conductive layer 11 does not cause any change in the other gas components in the gas mixture; thus free oxygen in the measured gas mixture is determined. Therefore a possible application, for example, is the monitoring of the condition of an exhaust gas catalyst for internal combustion engines, but of course also in other fields, for example thermal engineering, etc.

2. Oxygen-ion-conductive layer 11 is not catalytically active in a material-specific manner; thus equilibrium oxygen is determined and the sensor according to the present invention can be used, for example, as a $\lambda$-probe.

3. Oxygen-ion-conductive layer 11 is catalytically active in a material-specific manner; therefore individual gas components that selectively interact physically/chemically with the oxygen-ion-conductive layer can be determined.

On the whole, sensor 32 can be fabricated with a small number of printing steps which are known and controllable as such, for example in silk-screen process. These structures can be applied to unfired elements and then be joined as individual components in the co-firing or in the post-firing process.

What is claimed is:

1. A measuring arrangement for analyzing gas components in a gas mixture, comprising:
    at least one electrochemical solid electrolytic test cell including at least one cathode;
    a selective oxygen-ion-conductive layer covering the at least one cathode and including a mixed-conductive ceramic material, the selective oxygen-ion-conductive layer being exposed to the gas mixture and being configured to conduct oxygen therethrough only in the form of oxygen ions; and
    an electrically nonconductive layer separating the at least one cathode from the selective oxygen-ion-conductive layer, the electrically nonconductive layer including particular portions which are permeable to gas, the gas-permeable portions being configured to conduct the oxygen conducted through the selective oxygen-ion-conductive layer to the cathode;
    wherein the cathode is separated from the gas mixture by the selective oxygen-ion-conductive layer and the electrically nonconductive layer.

2. The measuring arrangement according to claim 1, further comprising:
    at least one further cathode,
    wherein the at least one cathode is situated in a diffusion channel between an opening of the diffusion channel and the at least one further cathode.

3. The measuring arrangement according to claim 2, wherein the diffusion channel is a tunnel structure composed of a heat-resistant glass.

4. The measuring arrangement according to claim 1, further comprising:
    at least one anode,
    wherein the at least one cathode and the at least one anode form an oxygen pump cell.

5. The measuring arrangement according to claim 4, wherein the at least one anode is situated in a diffusion channel.

6. The measuring arrangement according to claim 1, wherein a pumping capacity of the selective oxygen-ion-conductive layer is defined by a thickness of the selective oxygen-ion-conductive layer.

7. The measuring arrangement according to claim 1, wherein the mixed-conductive ceramic material is composed of one of a perovskite material and elpasolite.

8. The measuring arrangement according to claim 7, wherein the mixed-conductive ceramic material is composed of one of $Gd_{0.7}Ca_{0.3}FeO_{3-\delta}$ and $La_{0.6}Sr_{0.4}Co_{0.8}Cu_{0.2}O_{3-\delta}$.

9. The measuring arrangement according to claim 1, wherein the selective oxygen-ion-conductive layer is catalytically active in a material-specific manner.

10. The measuring arrangement according to claim 1, wherein the measuring arrangement is heated by a heating device.

* * * * *